United States Patent [19]
Yang

[11] Patent Number: 5,251,334
[45] Date of Patent: Oct. 12, 1993

[54] ANTI-DAZZLING DEVICE

[76] Inventor: Chen Y. Yang, 11912 Riding Loop Ter., North Potomac, Md. 20878

[21] Appl. No.: 724,640

[22] Filed: Jul. 2, 1991

[30] Foreign Application Priority Data

Jul. 10, 1990 [CN] China .............. 90104564.0

[51] Int. Cl.$^5$ .............................................. A61F 9/00
[52] U.S. Cl. .............................................. 2/15; 2/12; 2/9
[58] Field of Search ............... 2/9, 10, 12, 15, 185 R, 2/199, 197, 171, 172, 173, 434, 438, 441, DIG. 11

[56] References Cited

U.S. PATENT DOCUMENTS

| | | |
|---|---|---|
| D. 141,255 | 5/1945 | Dannenberg . |
| D. 168,736 | 2/1953 | Cooper et al. . |
| D. 277,995 | 3/1985 | Hand, Jr. . |
| D. 282,405 | 2/1986 | De Lozada . |
| D. 296,031 | 6/1988 | Coy et al. . |
| 779,591 | 1/1905 | Fairbanks ................... 2/10 |
| 1,502,820 | 7/1924 | Funk . |
| 1,575,219 | 3/1926 | McClay et al. . |
| 1,706,667 | 3/1929 | Haustein . |
| 1,790,328 | 1/1931 | Savage ...................... 2/12 |
| 1,803,338 | 5/1931 | Magee ....................... 2/12 |
| 1,960,450 | 5/1934 | Moore ....................... 2/12 |
| 2,388,626 | 11/1945 | Wilson . |
| 2,434,076 | 1/1948 | Kilhan ....................... 2/10 |
| 2,449,303 | 9/1948 | Laing . |
| 2,460,373 | 2/1949 | Waldman ................. 2/12 X |
| 2,481,960 | 9/1949 | Wall et al. . |
| 2,634,416 | 4/1953 | Fehrs . |
| 2,717,385 | 9/1955 | Linster ....................... 2/10 |
| 2,788,523 | 4/1957 | Seguin ....................... 2/12 |
| 3,049,716 | 8/1962 | Stegeman . |
| 3,212,102 | 10/1965 | Muller . |
| 3,383,707 | 5/1968 | McNeill . |
| 3,416,195 | 12/1968 | Borthwick ................ 24/303 |
| 3,631,539 | 1/1972 | Massa ..................... 2/197 X |
| 3,820,164 | 6/1974 | Kiebala ...................... 2/10 |
| 4,057,852 | 11/1977 | Contant ..................... 2/12 |
| 4,298,991 | 11/1981 | Recenello . |
| 4,393,519 | 7/1983 | Nicastro . |
| 4,481,681 | 11/1984 | Hankin ..................... 2/197 |
| 4,541,125 | 9/1985 | Phillips . |
| 4,630,317 | 12/1986 | Brown et al. ............ 2/171 X |
| 4,726,074 | 2/1988 | Baclit et al. . |
| 4,811,430 | 3/1989 | Janusz . |
| 4,839,924 | 8/1989 | Laurence .................... 2/10 |
| 4,852,189 | 8/1989 | Duggan . |
| 4,856,109 | 8/1989 | Desy et al. .................. 2/9 |
| 4,867,178 | 9/1989 | Smith ......................... 2/9 |
| 4,924,526 | 5/1990 | Parissenti et al. ....... 2/15 X |
| 4,955,087 | 9/1990 | Perez et al. ............... 2/9 X |

FOREIGN PATENT DOCUMENTS 410751  5/1934  United Kingdom ............. 2/10

*Primary Examiner*—Clifford D. Crowder
*Assistant Examiner*—Jeanette E. Chapman
*Attorney, Agent, or Firm*—James A. Wong

[57] ABSTRACT

An anti-dazzling device relating to eye protection for drivers driving at night comprises a fixing means, a shield, and an adapter means, in which the fixing means can be fixed adjustably in tightness to the head of a user, the adapter means extends forward from the fixing means, the shield is connected to the fixing means through the adapter means and is put at the left front or right front side of the user's eyes with its one end away from the user's eyes inclining to the centerline. The shield is made of transparent color material, which not only shields the intense dazzle emitting obliquely from head-on approaching cars but also does not hamper the normal sight of the users. Said device further comprises a front shield. The present invention is simple in structure, convenient for use and very low in cost.

10 Claims, 6 Drawing Sheets

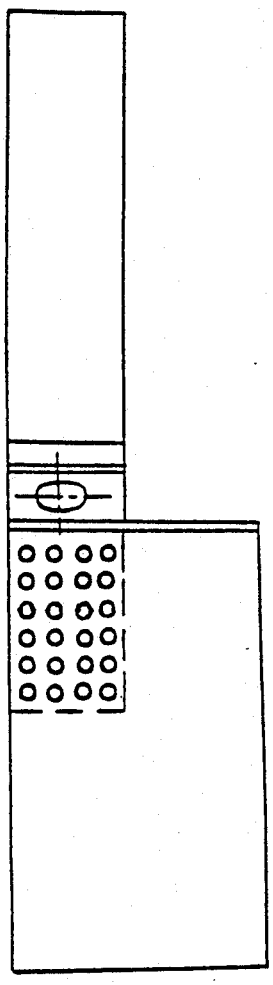
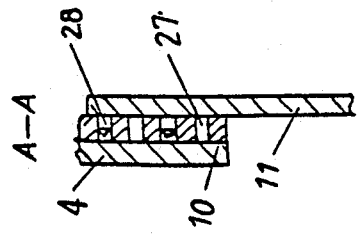
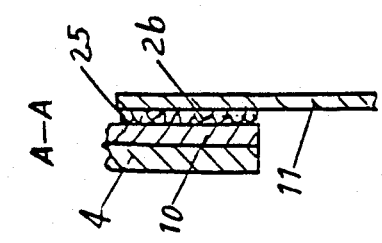
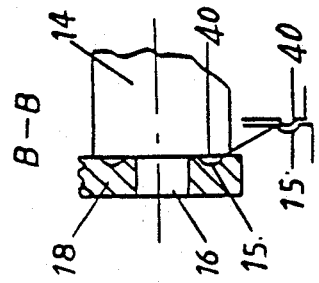
Fig. 4
Fig. 5
Fig. 6
Fig. 7

ANTI-DAZZLING DEVICE

BACKGROUND OF THE INVENTION

The present invention relates to an eye protection device. More particularly, it relates to a device to protect drivers or passengers at night against dazzling light from cars approaching head-on.

During driving at night, the headlight from head-on cars is very dazzling and intensely irritates eyes of the driver and passengers. Although the main headlights of cars may be switched to low beams, such light is still quite intense, particularly during heavy traffic at night. With head-on cars approaching one after the other and under incessant irritation of intense light, eyes of driver and passengers will be tired easily. If the driver is to wear tinted goggles to protect eyes, it will be difficult to perceive the road condition since it is dim at night and the tinted goggles further handicap the sight of the driver. Traffic accidents will be likely to occur. In order to overcome the above-mentioned difficulty, U.S. Pat. Nos. 4,541,125; 3,049,716; 3,212,102; and 3,383,707 propose several forms of shielding devices for eye protection. The common aspect of these shielding devices is ease of placing them in front of eyes and removing them therefrom. The shielding device is to be placed in front of eyes when the cars approach and then removed as soon as they pass each other. Such devices known heretofore do not completely solve the problem. Although such devices may enable a driver to avoid eye irritation from dazzle when the shield is placed in front of his or her eyes as a car approaches, the sight of the driver is obstructed from clearly perceiving the road condition and a traffic accident is likely to occur. Even with existing traffic regulations requiring a driver driving a car at night to immediately switch the main headlight to a low beam when another car approaches from a head-on direction, the driver simultaneously desires to place the shield in front of his or her eyes, and after the car passes, it is necessary to switch the low beam back to main headlight and to remove the shield from in front of his eyes without delay. Such frequent manipulation may inconvenience the driver, divert his attention, and result in a road accident. In view of the foregoing, it appears that the devices known heretofore do not satisfactorily solve the problem by preventing dazzling during driving at night.

OBJECTS OF THE INVENTION

An object of the present invention is to provide a new and improved form of anti-dazzling device which will enable a user to avoid eye irritation by dazzle from cars approaching head-on without obstructing the sight of the user.

Another object of the present invention is to provide a form of anti-dazzling device which is convenient to use and also simple in structure and low in cost.

Through long range and careful observation and experimentation, the inventor has discovered that the headlights of cars approaching head-on constitute a dazzling irritation to the driver or passengers as two cars meet, and such dazzle comes from the left front side, not from the immediate front, to irritate the driver or passengers. The foregoing is based upon traffic regulations requiring vehicles to be driven on the right side of the road. Thereupon, it is only necessary to place a shield obliquely at the left side of eyes of the driver or passengers with the front end of the shield inclining to the middle, thus the object of obstructing dazzle from head-on vehicles without affecting the sight of the driver can be achieved. Since there is no shield disposed in the immediate front, any frequent manipulation of the shield is unnecessary.

Thus, according to the inventive concept disclosed herein, there is provided a form of anti-dazzling device comprising an attaching member for fixing the anti-dazzling device to the head of a user, a transparent color side shield, and a coupling member for connecting a transparent color side shield and attaching member together and to place the transparent color side shield to one side of user's eyes. As an alternative form of the anti-dazzling device, it may comprise a transparent color front shield with means enabling it to be placed in front of user's eyes, and a coupling member with an adjustable support for placing the front shield in front of user's eyes.

In comparison with the prior art, the present invention has distinct advantages. It will arrive at the object to prevent irritating dazzle during driving at night and not to obstruct user's normal sight. The front shield is able to prevent any intense light of cars following behind from irradiating in the rear view mirror inside the car and then reflecting into the driver's eyes and also to protect the driver from the braking light emitting from the car in front during driving at night. In the daytime, it can be used in place of sun glasses. The present invention is simple in structure, convenient for use, and low in cost.

BRIEF DESCRIPTION OF THE DRAWINGS

FIG. 4 is a front view of the anti-dazzling device of FIG. 1;

FIG. 5 is a sectional view in part taken along "B—B" in FIG. 2;

FIG. 6 is a sectional view in part taken along "A—A" in FIG. 4 showing one form of joining of the side shield with the rotatable plate;

FIG. 7 is a sectional view in part taken along "A—A" in FIG. 4 showing another form of joining of the side shield with the rotatable plate;

DETAILED DESCRIPTION OF THE INVENTION

Referring now in detail to FIGS. 1-6 of the accompanying drawings, the reader will readily discern the preferred embodiment of the present invention.

Figure 1:
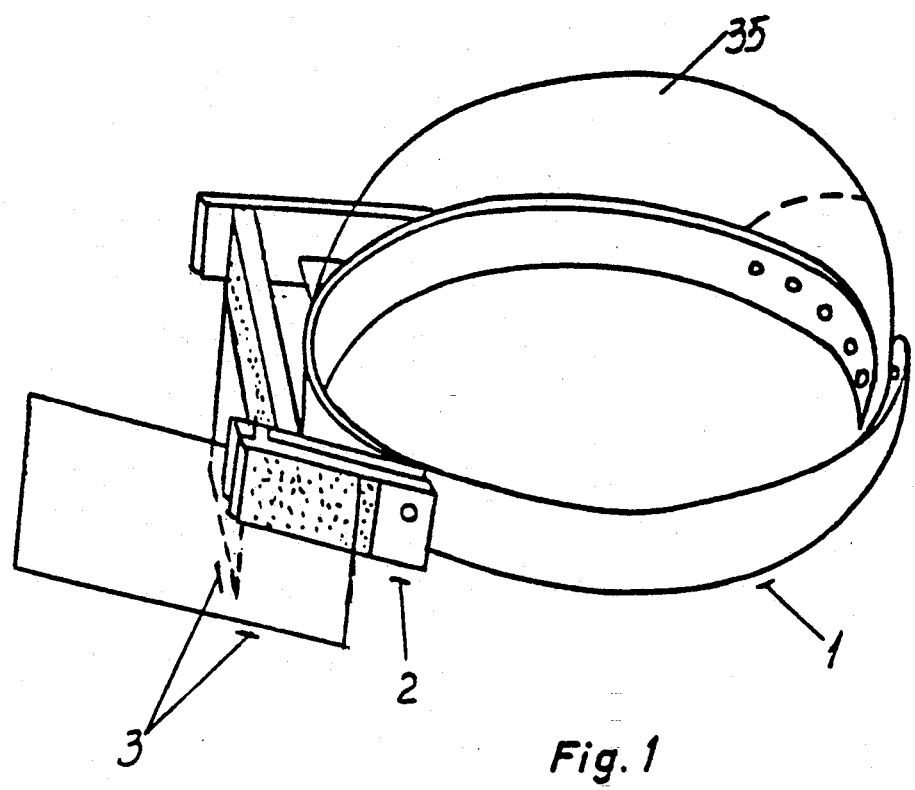
FIG. 1 is a view in perspective of a preferred form of the anti-dazzling device of the present invention.

As may be seen in FIG. 1, the disclosed anti-dazzling device comprises a band or strap 1 for securing the device on the head of a user, a shield 3, and an adapter 2 for connecting the shield 3 to the band or strap and to place the shield 3 on the left side and forwardly of the user's eyes.

Figure 2:
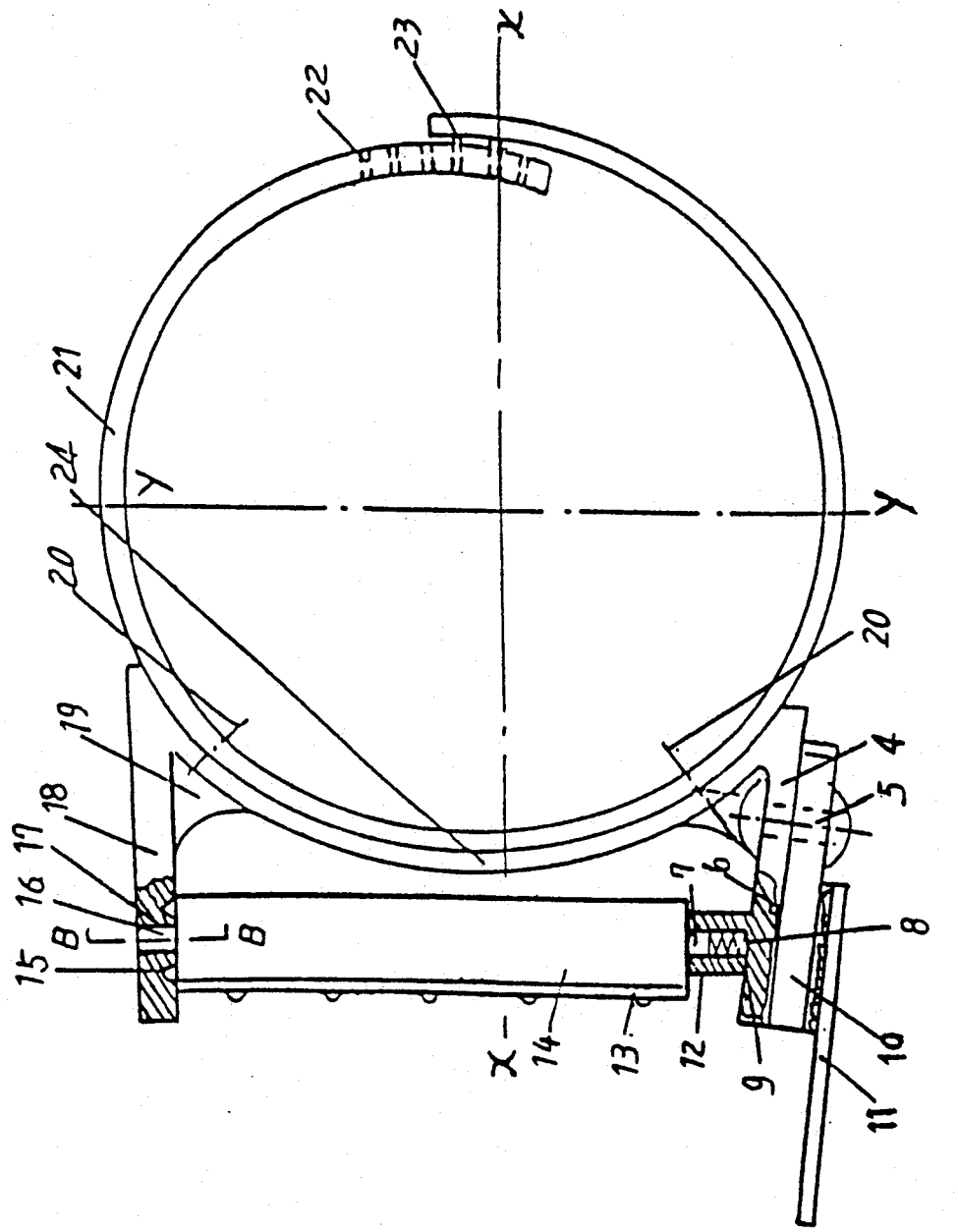
FIG. 2 is a top plan view of the anti-dazzling device of FIG. 1.

As may be seen in FIG. 2, the band or strap 1 comprises a head hoop 21 made of an elastic and flexible strip which can be of plastic, leather or canvas band and is adjustable in size diametrically. Hoop 21 is formed at the rear with two separate ends, one of which has a row of holes 22. The other end is provided with a nipple 23. The nipple 23 can be forcibly pushed into any one of the holes 22 to control the size of hoop 21. The size of the head hoop 21, adjusted as described above, by pushing nipple 23 into different holes 22, will provide a snug fit onto different size heads. This adjustment feature of hoop 21 can also be made in the form of a belt buckle or an elastic cord. As an alternative, the head hoop 21 can be adapted to a cap 35 to form part of a hat as illustrated in FIG. 1.

The adapter 2 includes a curved base 24 with a curvature to fit the forehead of a user. At each end of the curved base 24, there is a forwardly extending rod, the right side rod 18 being parallel to centerline X—X and the left side rod 4 extending obliquely to include an angle preferably of about 11° with centerline X—X. A web 19 is provided between rod 18 and curved base 24 as reinforcement. A similar reinforcement is provided between rod 4 and curved base 24. A rotatable plate 10 is supported on one side of the left side rod 4 and assembled on it through a rotatable shaft 5 about which the rotatable plate 10 can rotate. The rotatable plate 10 carries a locating teat 6 which may sit on top of the left side rod 4 when the rotatable plate 10 is rotated to a horizontal position and held at that position. When the rotatable plate 10 is rotated backward, the locating teat 6 will seat on the head hoop 21 and keep the rotatable plate 10 at a position on top of the head to the rear.

As may be seen in FIGS. 6-7, a side shield 11 is securely attached on the rotatable plate 10 through a coupling assembly. The side shield 11 is made of transparent color material and is rectangular in shape. The assembly may be a nap and hooklet agraffe type or a nipple and hole snap type. The so-called nap and hooklet agraffe refers to a commercially available agraffe means composed of a piece of napped fabric with a plurality of elastic ringlets and a piece of hooklet band with a plurality of elastic hooklets which agraffe means with ringlets and hooklets constitutes what is commonly known as Velcro. When the nap piece and the hooklet piece are pressed together, many hooklets will be forced into ringlets and the two pieces are attached together to positively effect a combined strength. When pulled upon by force, the hooklets can be withdrawn from the ringlets due to the elasticity of both. The attached pieces will then be separated. As may be seen in FIG. 6, the coupling assembly using such nap and hooklet agraffe comprises a hooklet band 26 consisting of a plurality of elastic hooklets adhered to the inner upper side of the side shield 11, and a layer of napped fabric 25 consisting of a plurality of elastic ringlets adhered to the outer side of the rotatable plate 10, or vice versa, so that the side shield 11 may be readily attached to the rotatable plate 10 or detached from it. As described, the position of the side shield 11 may be adjusted to forward, backward, upward, or downward positions. As may be seen in FIG. 7, a nipple and hole snap type coupling assembly may also be used. A number of nipples 28 are provided on the inner upper side of side shield 11 and several rows of equidistant holes 27 of equal diameter to that of the nipples 28 are provided on rotatable plate 10 so that side shield 11 can be secured to rotatable plate 10 by snapping nipples 28 into one set of holes 27 or into a different set of holes 27. The position of the side shield 11 can thus be adjusted forwardly, backwardly, upwardly, or downwardly.

As may be seen in FIG. 2, a boss 12 extends on the upper inner side of left side rod 4 to the right side rod 18. The end surface of boss 12 is parallel to the inner side surface of right side rod 18. Centrally of boss 12 there is a counterbore 9. A drilled hole 17 extends in the right side rod at a position opposite counterbore 9, with hole 17 and counterbore 9 being in coaxial relationship.

As may be seen in FIGS. 2 and 5, four locating dents 15 are provided on the inner side of right side rod 18, distributed around the circumference of a circle with the hole 17 as its center, with one pair of dents in the horizontal position and the other pair in the vertical position.

It is also seen in FIGS. 2 and 5 that coaxial rotatable shafts 7, 16 are provided at both ends of rotatable member 14, with diameters compatible with that of counterbore 9 and hole 17. Two locating bumps 40 are provided on the side surface of rotatable member 14 adjacent to the right side rod 18. A compression spring 8 is disposed in counterbore 9. Rotating shafts 7, 16 of rotatable member 14 are disposed in counterbore 9 and hole 17, respectively. Under the action of compression spring 8, the right end of rotatable member 14 presses tightly against the inner side surface of right side rod 18, and when rotatable member 14 is turned to a horizontal or vertical position, locating bumps 40 will just stick into locating dents 15 so as to hold the rotatable member 14 in the horizontal or vertical position, respectively.

Figure 3:
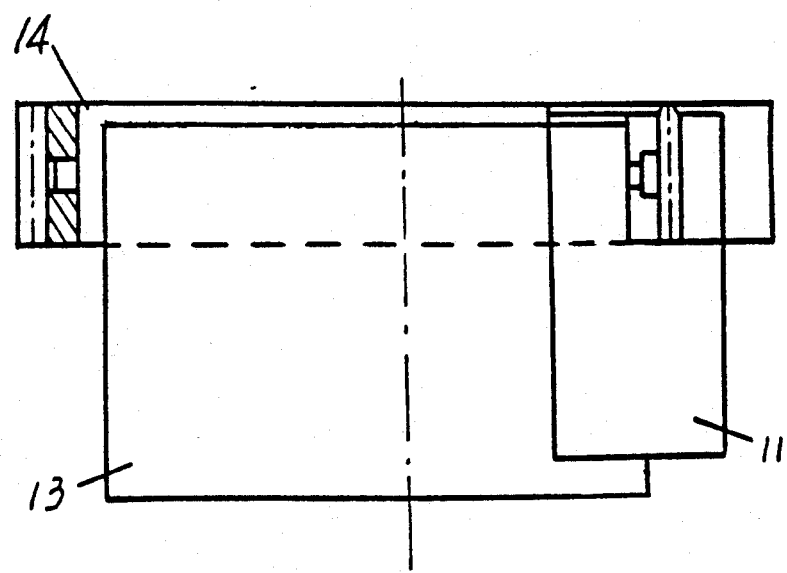
FIG. 3 is a left elevational side view of the anti-dazzling device of FIG. 1.

As may be seen in FIGS. 2 and 3, a front shield 13 made of transparent color material is securely attached to the front side of rotatable member 14 by means of a coupling assembly of either nap and hooklet agraffe type 25, 26 or nipple and hole snap type 27, 28 similar to that for securing side shield 11 and rotatable plate 10. No further explanation is believed to be necessary with respect to the foregoing. The adapter or connector means 2 and band or strap 1 are connected together by rivets or other fastenings 20.

As an alternative, the right side rod 18, rotatable member 14, and front shield 13 may be omitted. Only the securing band or strap 1 and the left side of adapter 2, i.e., left side rod 4, rotatable shaft 5, rotatable plate 10 and side shield 11 are retained. Further simplification may be made to the above-mentioned alternative by combining rotatable plate 10 and left side rod 4 into one piece and keeping the side shield 11 fixed, while the function of anti-dazzling will still be realized just as well.

The device of the embodiment as described is used by putting the head hoop 21 securely on the head, attaching side shield 11 onto rotatable plate 10 and adjusting it to a position capable of shielding any dazzle coming head-on, or turning the side shield 11 to the top of the head to remove it from a position of use when it is not needed. During daylight driving, the front shield 13 may be used to shield strong sunlight. It is only necessary to attach the front shield 13 to the front of rotatable member 14 and adjust it to a position capable of shielding sunlight. When not needed, the front shield 13 is rotated to a horizontal position or to top of head, or remove it from a position of use. The disclosed device is not only useful while driving, but also useful in watching athletic games, in outdoor activities, or in preventing strong glare from ice and snow.

Figure 8:
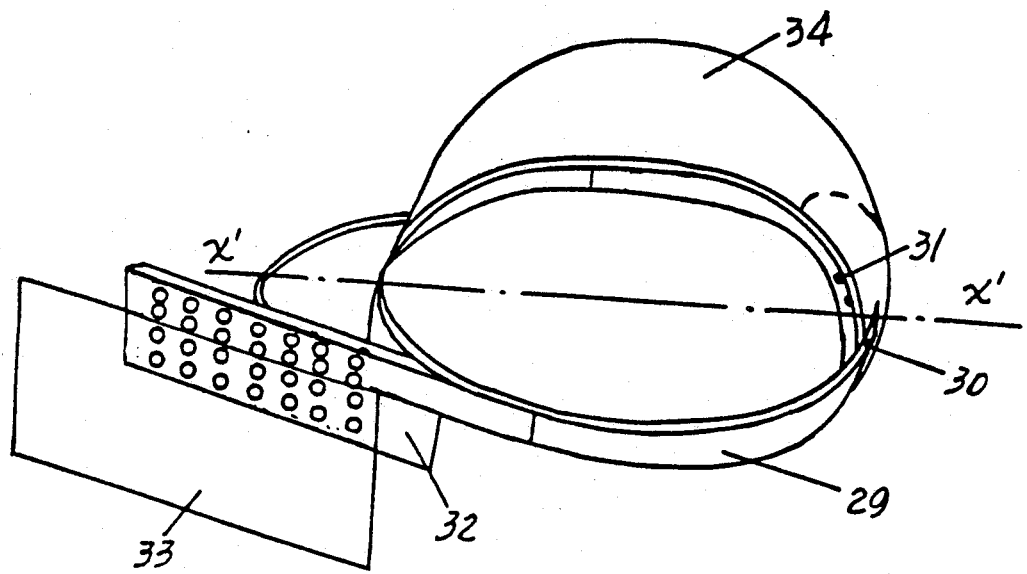
FIG. 8 is another embodiment of an anti-dazzling device according to the present invention.

As shown in FIG. 8 is a simplified embodiment of the present invention wherein a head hoop 29 with both ends carrying a diameter adjustment mechanism. An opening is cut at the rear end of hoop 29. At one end of the opening is a row of holes 31 and at the other end are nipples 30 which can be snugly pushed into holes 31. By pushing nipples 30 into different holes 31, the size of head hoop 29 can be adjusted so as to be securely placed on the head of users of different size and shape. The diameter adjustment mechanism can be made in the form of a belt buckle or an elastic cord. The head hoop 29 may be made of plastic strip, leather strip or canvas strip and the like of proper stiffness but with elasticity and flexibility. At the left side of head hoop 29 is a connecting rod 32 extending forward inclining to centerline X'—X' and forming an included angle, 11° or as otherwise preferred, with the centerline X'—X'. A side shield 33 made of transparent color material is securely attached to the side surface of a connecting rod 32. The coupling assembly between the two may be of nap and hooklet agraffe type 25, 26 or nipple and hole snap type 27, 28, as that for assembling side shield 11 and rotatable plate 10 together in the above-mentioned embodiment. No further explanation of the foregoing appears to be necessary herein.

Figure 9:
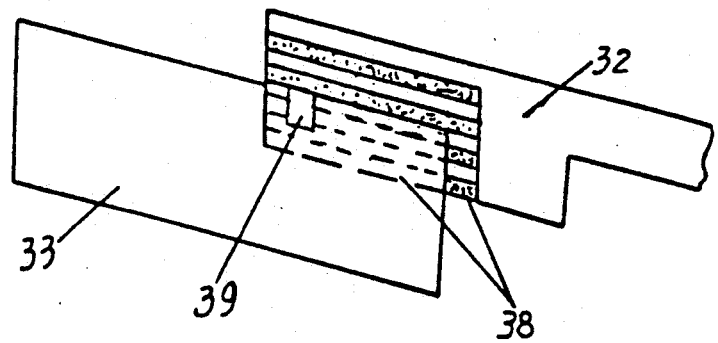
FIG. 9 is another form of joining the side shield with connector member of the anti-dazzling device as shown in FIG. 8.
Figure 10:
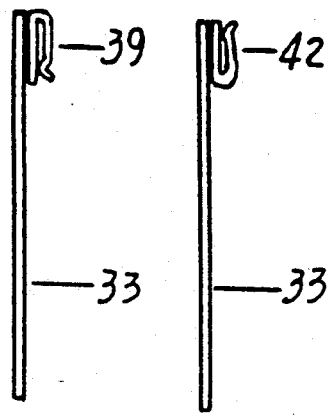
FIGS. 10a and 10b show two forms of clip hooks on an enlarged scale use in joining the side shield as shown in FIG. 9.

As may be seen in FIG. 9, a further form of attaching side shield 33 to connecting rod 32 is disclosed. On connecting rod 32 several parallel strips 38 are provided with clearance between connecting rod 32 and with their ends fixed to the connecting rod 32. On the right upper part of side shield 33 is provided a bent-downward clip hook 39, as shown in FIG. 10a, which can be inserted into the clearance between strips 38 and connecting rod 32 and clamp of one of the strips 38. It is also possible to adopt a bent-upward clip hook 42, as shown in FIG. 10b, so as to secure the side shield 33 to a desirable position by the same means. As a further alternative, a piece of magnetic material is provided on the right upper part of side shield 33 and the same on the connecting rod 32, so that the side shield 33 will be attracted to the connecting rod 32.

A thin web may be used between connecting rod 32 and the front part of head hoop 29 for strengthening, forming a visor as an alternative type. In case of putting an additional cap 34 on the head hoop 29, a hat is then formed.

Figures 11, 12:
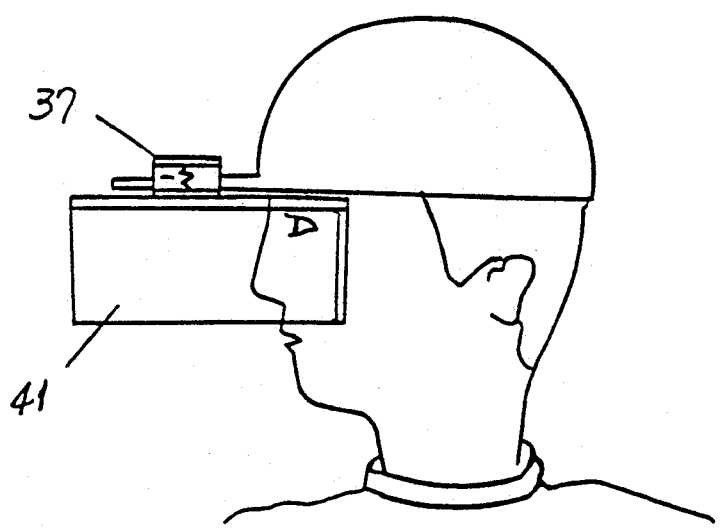
FIG. 11 is a further embodiment of an anti-dazzling device according to the present invention.
FIG. 12 is a side shield with clamp of the embodiment as shown in FIG. 11.

As may be seen in FIG. 11, a still further embodiment of the present invention is disclosed. The securing mechanism of an anti-dazzling device to be worn on the head of a user is a hat with visor. As may be seen in FIG. 12, side shield 41 is to be understood to be of a transparent color plate with rectangular or near rectangular flange 36. In the middle of flange 36, a clamp 37 is secured by screw fitting, riveting or adhesion. The dimension of shield 41 may be about 5 inches high and about 10 inches wide in the form of a rectangle. However, with the differences in size of the heads, shield 41 is to be in several sizes. While in use, the side shield 41 with clamp 37 is clipped to the visor and placed at the left front side of the eyes so as to shield any dazzle from head-on direction but not to obstruct the sight of the user. If this shield 41 is placed immediately in front of the eyes, i.e., clipped in front of visor, it will be a front shield and will function the same as the above-mentioned front shield 13. In this way, during nighttime driving, it will prevent intense light reflected from the rear-view mirror inside the car from cars following behind which otherwise would irritate the driver's eyes and also prevent the intense irritating light from cars ahead at braking. By daylight it can be used as sun glasses.

The embodiments presented above are applicable to traffic regulations which require vehicles to be driven on the right side of the road. As for traffic regulations which require vehicles to be driven on the left side of the road, it is only necessary to place the shielding mechanism 3 and the adapter 2 on the right front side of the user's head.

What is claimed is:

1. An anti-dazzling device for protecting the eyes of a motor vehicle operator from strong light and/or glare of oncoming vehicles, said device having in position of use a left side, a right side, a front side, and a rear side with a centerline X—X between the left and the right sides, said device comprising in combination a shield, securing means, and adapter means:

wherein said securing means secures said shield on the head of a vehicle operator or other use, said adapter means connects said shield and said securing means to each other, said adapter means extending forward from one side of said securing means at an angle to said centerline X—X, said adapter means includes a coupling assembly connecting said shield at one side thereof so that it is placed at one side of the operator's eyes to hold one end of the shield inclined to the centerline X—X away from the eyes;

wherein said device comprises a further shield to be placed in front of the user's eyes and said adapter means has an additional coupling assembly holding said further shield in front;

wherein said securing means is a head hoop (21) of adjustable diameter, said adapter means is formed with a curved base (24), a left side rod (4) extending forward from the left end of the curved base (24) inclining to said centerline X—X, a rotatable plate (10) rotatable around a rotatable shaft (5) and being securely attached to a side surface of the left side rod (4), said first recited shield (11) being securely attached to the side surface of the rotatable plate and adjustably connected therewith through different positions of said rotatable plate.

2. The anti-dazzling device according to claim 1, wherein said coupling assembly comprises hook and loop pile fasteners (25, 26).

3. The anti-dazzling device according to claim 1, wherein said coupling assembly comprises a nipple and hole snap type structure (27, 28).

4. The anti-dazzling device according to claim 1, wherein said additional coupling assembly of said adapter means further has a right side rod (18) extending forward from the right end of curved base (24) and parallel to the centerline X—X, a hole (17) and locating dents (15) on the right side rod, a boss (12) and a counterbore (9) on the left side rod, a compression spring (8) disposed in said counterbore (9), a rotatable member (14) having locating bumps (40) thereon and rotatable shaft portions (16, 7) disposed in the counterbore (9) and said hole (17) and whereby through said rotatable shafts (16, 7), said locating bumps (40) for cooperation with said locating dents (15) on the right side of said rotatable member (14), the front shield being securely attached on the outer side surface of the rotatable member (14) and the front shield and said rotatable member are moved together through adjustable positions.

5. The anti-dazzling device according to claim 2, wherein said securing means is connected to a cap (35).

6. The anti-dazzling device according to claim 3, wherein said securing means is connected to a cap (3).

7. The anti-dazzling device according to claim 4, wherein said coupling assembly comprises hook and loop pile fasteners (25, 26).

8. The anti-dazzling device according to claim 4, wherein said coupling assembly comprises a nipple and hole snap type structure (27, 28).

9. The anti-dazzling device according to claim 7, wherein said securing means is connected to a cap (35).

10. The anti-dazzling device according to claim 8, wherein said securing means is connected to a cap (35).

* * * * *